United States Patent
Ikegawa et al.

(10) Patent No.: US 7,244,859 B2
(45) Date of Patent: Jul. 17, 2007

(54) METHOD FOR PRODUCING δ-AMINOPENTADIENOATE DERIVATIVES

(75) Inventors: Akihiko Ikegawa, Kanagawa (JP); Masuji Motoki, Kanagawa (JP); Katsuyoshi Yamakawa, Kanagawa (JP)

(73) Assignee: Fujifilm Corporation, Tokyo (JP)

( * ) Notice: Subject to any disclaimer, the term of this patent is extended or adjusted under 35 U.S.C. 154(b) by 0 days.

(21) Appl. No.: 10/395,166

(22) Filed: Mar. 25, 2003

(65) Prior Publication Data
US 2003/0181483 A1   Sep. 25, 2003

(30) Foreign Application Priority Data
Mar. 25, 2002   (JP) ............................. 2002-083410

(51) Int. Cl.
*C07C 299/00*   (2006.01)
*C07D 207/04*   (2006.01)

(52) U.S. Cl. ...................... 560/155; 548/570
(58) Field of Classification Search ................ 560/172; 548/570
See application file for complete search history.

(56) References Cited

U.S. PATENT DOCUMENTS

| | | | |
|---|---|---|---|
| 2,165,339 A | 7/1939 | Brooker | |
| 2,186,608 A | 1/1940 | Keyes | |
| 4,886,835 A * | 12/1989 | Malleron et al. | 514/532 |
| 4,971,979 A * | 11/1990 | Malleron et al. | 514/315 |

FOREIGN PATENT DOCUMENTS

JP   58-181041   10/1983

OTHER PUBLICATIONS

Nair et al, Journal of Organic Chemistry, 1981, vol. 46, pp. 4759 to 4765.*
Izevestiya Akademii Nauk SSSR, Seriya Khimicheskaya, 5, p. 1060-4, 1981. p. 1 (abstract page ).*
Nair, Vasu et al,Tetrahedron Letters, 1980, Vo. 21, pp. 3155-3158.

* cited by examiner

*Primary Examiner*—Taylor Victor Oh
(74) *Attorney, Agent, or Firm*—Birch, Stewart, Kolasch & Birch, LLP

(57) ABSTRACT

The invention is a method for producing δ-aminopentadienoate derivatives of formula (1), the method comprising reacting a streptocyanine derivative of formula (2) with an ester derivative of formula (3) in the presence of an organic base. In formulae (1) to (3), $R^1$ represents an alkyl group or an aryl group; $R^2$, $R^3$, $R^4$ and $R^5$ independently represent a hydrogen atom or an alkyl group; $R^2$ and $R^3$, or $R^4$ and $R^5$ may bond to each other to form a ring; Y represents an electron attractive group; X represents an acid radical; n indicates 0 or a positive number, which is no more than 5; Y may bond to $R^1$ to form a ring

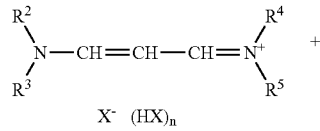

Formula (2)

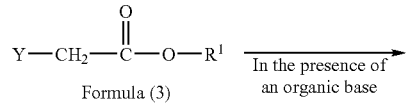

Formula (3)

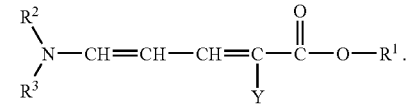

Formula (1)

21 Claims, No Drawings

METHOD FOR PRODUCING δ-AMINOPENTADIENOATE DERIVATIVES

BACKGROUND OF THE INVENTION

1. Field of the Invention

The present invention relates to an economical and safe method for producing on an industrial-scale specific δ-aminopentadienoate derivatives that are useful, for example, as UV absorbents.

2. Description of the Related Art

Methods of producing δ-aminopentadienoate derivatives have been known for a long time. For example, F. M. Harmer, *Heterocyclic Compounds-Cyanine Dyes and Related Compounds* (John Wiley & Sons, New York and London, 1964), Chapter XIII, page 491, and U.S. Pat. No. 2,165,339 and U.S. Pat. No. 2,186,608 disclose methods of producing δ-aminopentadienoate derivatives via dianil derivatives. However, the reaction path of the disclosed methods is long and the overall yield is low.

On the other hand, *Tetrahedron Letters*, Vol. 21, page 3155 (1980) discloses a method of producing δ-aminopentadienoate derivatives by reacting a streptocyanine derivative with a carbonyl compound in the presence of sodium hydride and triethylamine. However, sodium hydride is flammable, and therefore, the method is unfavorable for industrial-production from the viewpoint of safety, and in addition, the yield of such a method is not sufficiently high.

From the above background art, a method using safe reagents for producing the derivatives in a shorter reaction path is desired.

SUMMARY OF THE INVENTION

The present invention is intended to solve the problems in the related art as above and to achieve the object of the invention which is to provide an economical and safe method for producing δ-aminopentadienoate derivatives on an industrial-scale.

The present inventors have assiduously studied methods using safe reagents and of a shorter reaction path, and, as a result, have found that, when a streptocyanine derivative, which is readily synthesized in one step, for example, from a 1,1,3,3-tetraalkoxypropane and an amine, is reacted with an ester derivative in the presence of an organic base, the desired δ-aminopentadienoate derivatives can be produced efficiently. On the basis of this finding, the present invention has been completed.

Specifically, the invention is a method for producing a δ-aminopentadienoate derivative of the following formula (1), the method comprising the step of; reacting a streptocyanine derivative of the following formula (2) with an ester derivative of the following formula (3) in the presence of an organic base

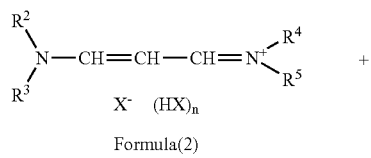

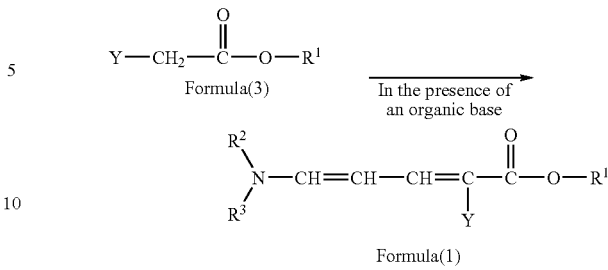

wherein in formulae (1)-(3), $R^1$ represents one of an alkyl group and an aryl group; $R^2$, $R^3$, $R^4$ and $R^5$ independently represent one of a hydrogen atom and an alkyl group; at least one of $R^2$ and $R^3$, and $R^4$ and $R^5$ may bond to each other to form a ring; Y represents an electron attractive group; X represents an acid radical; n indicates one of 0 and a positive number of no more than 5; Y may bond to $R^1$ to form a ring.

DETAILED DESCRIPTION OF THE PREFERRED EMBODIMENTS

The method of the present invention for producing δ-aminopentadienoate derivatives of formula (1) comprises reacting a streptocyanine derivative of formula (2) with an ester derivative of formula (3) in the presence of an organic base. The method of the invention for producing such δ-aminopentadienoate derivatives is advantageous in that the reagents to be used are safe, the intended products can be produced in a shorter reaction path, and therefore the method is safe, economical and suitable to industrial-scale plants.

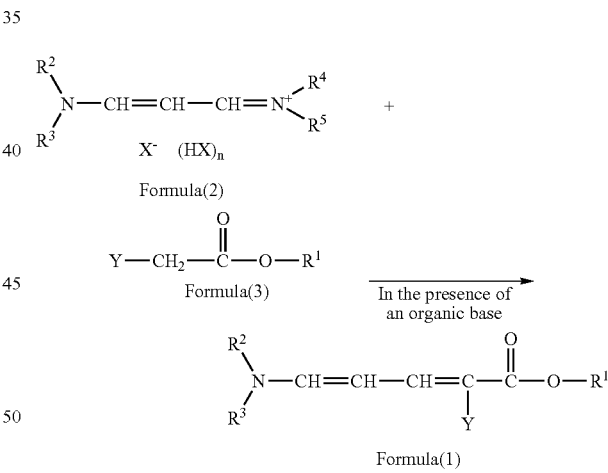

In formulae (1) to (3), $R^1$ represents an alkyl group or an aryl group; $R^2$, $R^3$, $R^4$ and $R^5$ independently represent a hydrogen atom or an alkyl group; Y represents an electron attractive group; X represents an acid radical; n indicates 0 or a positive number of no more than 5.

The alkyl group represented by $R^1$ preferably has from 1 to 30 carbon atoms, and more preferably from 1 to 25 carbon atoms. Examples thereof include methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl and eicosyl groups. They may be branched.

The aryl group represented by $R^1$ preferably has from 6 to 20 carbon atoms, and more preferably from 6 to 15 carbon atoms. Examples thereof include phenyl, p-tolyl, p-chlorophenyl, α-naphthyl and β-naphthyl groups.

The alkyl group represented by $R^2$, $R^3$, $R^4$ and $R^5$ preferably has from 1 to 20 carbon atoms, and more preferably from 1 to 10 carbon atoms. Examples thereof include methyl, ethyl, propyl, butyl, pentyl, hexyl, heptyl, octyl, nonyl and decyl groups. $R^2$ and $R^3$, and/or $R^4$ and $R^5$ may bond to each other to form a ring. The ring is preferably a 5- to 8-membered, and more preferably 5- or 6-membered ring. Examples thereof include pyrrolidine, piperidine, piperazine, morpholine, thiomorpholine and isoindoline rings. The ring may be substituted and may be condensed with another ring (e.g., benzene ring).

Examples of the acid radical represented by X include acetate, hydrochloride, sulfate, bromide, iodide, perchlorate, p-toluenesulfonate and methanesulfonate radicals. Most preferably, it is an acetate radical.

The variable "n" is preferably 1.

The electron attractive group in Y means a substituent having a Hammett constant σp value of 0 or more, and a substituent having a σp value of 0.2 to 1.0 is preferable, and a substituent having a σp value of 0.3 to 0.9 is more preferable. Examples of the electron attractive group include an alkylsulfonyl group, an arylsulfonyl group, an acyl group, an arylcarbonyl group, a cyano group, an alkoxycarbonyl group, an aryloxycarbonyl group, a formyl group, a trifluoromethoxy group, a trifluoromethylthio group, an alkylcarbamoyl group, an arylcarbamoyl group, an alkylsulfinyl group, an arysulfinyl group, an alkylsulfamoyl group, an arylsulfamoyl group, a trifluoromethyl group, and a nitro group.

Preferred examples of the electron attractive group represented by Y include an alkanesulfonyl group, an arenesulfonyl group, an acyl group, an arylcarbonyl group, a cyano group, an alkoxycarbonyl group and an aryloxycarbonyl group. These groups are described further. Typical examples thereof include an alkanesulfonyl group preferably having 1 to 20, more preferably 1 to 8 and still more preferably 1 to 4 carbon atoms (e.g., methanesulfonyl, ethanesulfonyl, butanesulfonyl and octanesulfonyl), an arenesulfonyl group preferably having from 6 to 20, and more preferably from 6 to 15 carbon atoms (e.g., benzenesulfonyl, p-toluenesulfonyl, p-chlorobenzenesulfonyl, and naphthalenesulfonyl); an acyl group preferably having from 1 to 20, and more preferably from 1 to 5 carbon atoms (e.g., formyl, acetyl, and propionyl); an arylcarbonyl group preferably having from 7 to 20, and more preferably from 7 to 15 carbon atoms; a cyano group; an alkoxycarbonyl group preferably having from 2 to 20, and more preferably from 2 to 9 carbon atoms (e.g., methoxycarbonyl, ethoxycarbonyl, t-butoxycarbonyl, and benzyloxycarbonyl); and an aryloxycarbonyl group preferably having from 7 to 20, and more preferably from 7 to 15 carbon atoms (e.g., phenoxycarbonyl, and p-nitrophenoxycarbonyl). Among them, an arenesulfonyl group having from 6 to 15 carbon atoms is preferable, and a benzenesulfonyl group is most preferable. The electron attractive group represented by Y may form a ring along with $R^1$.

Specific examples of the compounds of formulae (1) to (3) are shown below, but the invention is not limited to these examples. Compounds 1-1 to 1-9 are examples of the δ-aminopentadienoate derivatives of formula (1); Compounds 2-1 to 2-5 are those of the streptocyanine derivatives of formula (2); and Compounds 3-1 to 3-6 are those of the ester derivatives of formula (3).

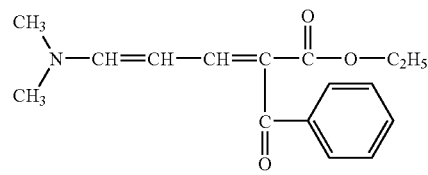
1-1

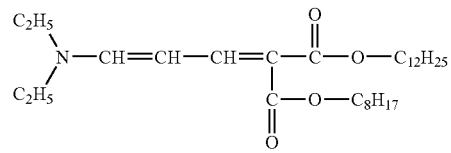
1-2

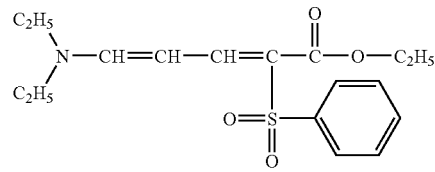
1-3

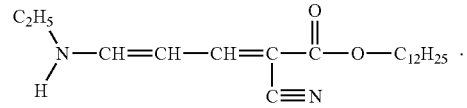
1-4

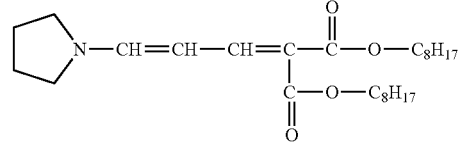
1-5

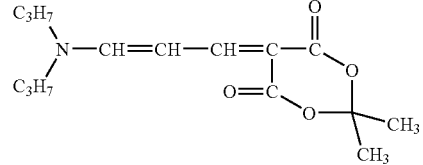
1-6

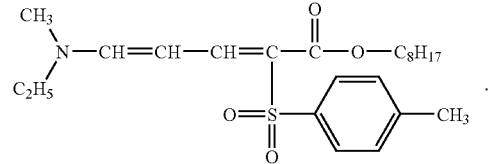
1-7

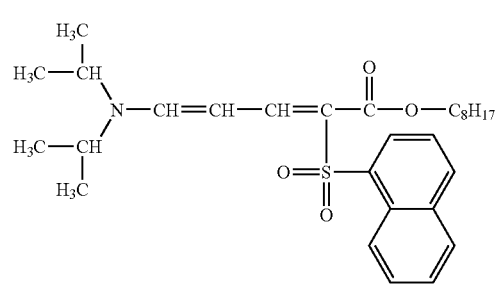
1-8

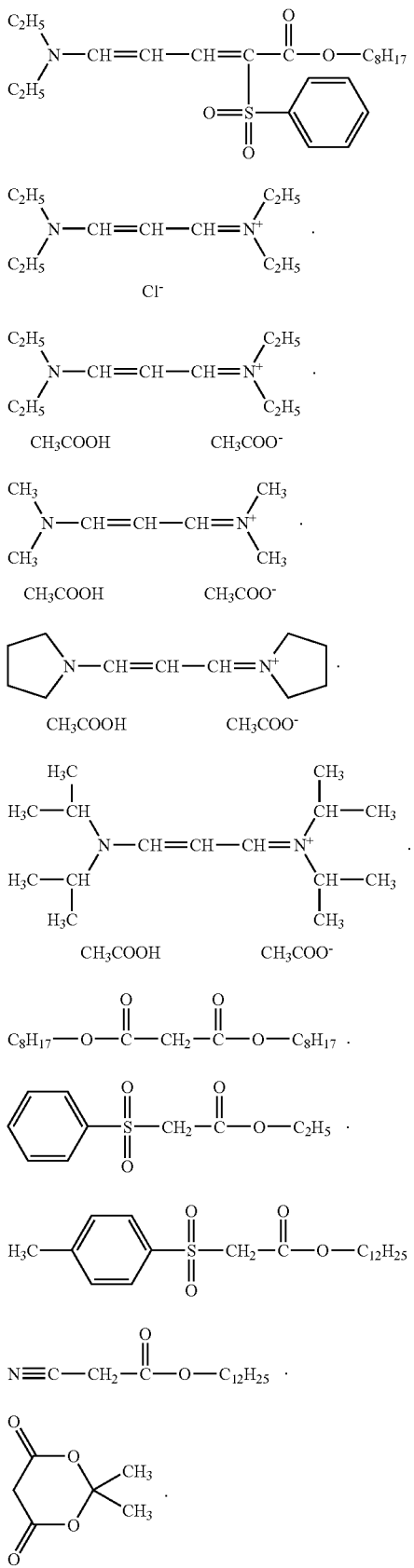

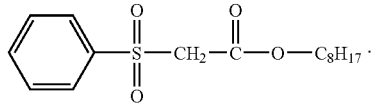

In the production method of the invention, the compound of formula (2) is reacted with the compound of formula (3) in the presence of the organic base. Typical examples of the organic base include alkoxides (e.g., sodium methylate, sodium ethylate, potassium t-butoxide), DBU (1,8-diazabicyclo[5.4.0]undec-7-ene), DBN (1,5-diazabicyclo[4.3.0]non-5-ene), and 1,1,3,3-tetramethylguanidine. Among those, more preferable are DBU (1,8-diazabicyclo[5.4.0]undec-7-ene), DBN (1,5-diazabicyclo[4.3.0]non-5-ene) and 1,1,3,3-tetramethylguanidine; and most preferable are DBU (1,8-diazabicyclo[5.4.0]undec-7-ene) and DBN (1,5-diazabicyclo[4.3.0]non-5-ene).

Reaction conditions in the production method of the invention will be described in detail.

When a streptocyanine derivative of formula (2) is reacted with an ester derivative of formula (3), the solvent to be used is preferably an organic solvent and more preferably an aromatic solvent such as toluene, and benzene; a hydrocarbon solvent such as hexane, and petroleum ether; an ester solvent such as ethyl acetate, and methyl acetate; an alcohol solvent such as methanol, ethanol, isopropanol, butanol, t-butanol, and ethylene glycol; an amide solvent such as dimethylformamide, dimethylacetamide, diethylacetamide, diethylpropionamide, and 1-methylpyrrolidone; an ether solvent such as diethyl ether, dioxane, and tetrahydrofuran; and a polar solvent such as dimethylsulfoxide. Most preferably, the solvent is any of dimethylformamide, dimethylacetamide, 1-methylpyrrolidone and dimethylsulfoxide.

The reaction temperature may be between −78° C. and the boiling point of the solvent used, but is preferably between 0° C. and 70° C., and more preferably between 0C. and 50° C.

The molar ratio of the organic base may be from 0.1 to 100 times, and preferably from 0.3 to 10 times, and more preferably from 0.5 to 3 times as many as the number n in formula (2), or that is, the number of mols of HX in the compound of formula (2).

The molar ratio of the ester derivative of formula (3) to the streptocyanine derivative of formula (2) may be from 0.1 to 100 times, and preferably from 0.3 to 50 times, and more preferably from 0.5 to 10 times, and most preferably from 0.8 to 2 times.

The amount (mass) of the solvent is from 0.5 to 20 times, and preferably from 1 to 10 times, and more preferably from 1 to 5 times as many as the mass of the streptocyanine derivative of formula (2).

The reaction end point may be confirmed, for example, through thin layer chromatography or high performance liquid chromatography. After the reaction, the product, δ-aminopentadienoate derivative of formula (1) may be obtained from the reaction mixture through ordinary product isolation by, for example, liquid-liquid separation, column chromatography, or crystallization by addition of a poor solvent to the reaction mixture.

EXAMPLES

The present invention will be described more specifically with reference to the following Examples, which, however, are not intended to restrict the scope of the invention.

Example 1

(Production of Compound 1-3)

15.0 g of 1,3-bis-diethylaminotrimethinium diacetate (Compound 2-2—this is obtained by heating 1,1,3,3-tetramethoxypropane, diethylamine and acetic acid followed by concentrating the reaction mixture), 30 ml of dimethylacetamide (solvent) and 11.32 g of ethyl benzenesulfonylacetate (Compound 3-2) were mixed with each other, and 15.1 g of DBU (organic base: 1,8-diazabicyclo[5.4.0]undec-7-ene) was added dropwise thereto. The resultant mixture was stirred at room temperature for 6 hours. Next, 60 ml of water and 3 ml of acetic acid were added to the reaction mixture and the resultant mixture was stirred while cooling with water, and the crystal precipitated was taken out through filtration and washed with water. The crude crystal thus obtained was recrystallized from isopropanol, and 1320 g of the intended product, ethyl 4-diethylamino-1-benzenesulfonylpentadienoate (Compound 1-3) was obtained. The yield was 78.9%; and the purity (HPLC area ratio) was 100.0%.

Comparative Example 1

(Production of Compound 1-3):

According to the method described in *Tetrahedron Letters*, Vol. 21, page 3155 (1980), 1,3-bis-diethylaminotrimethinium diacetate, sodium hydride, ethyl benzenesulfonylacetate and triethylamine were reacted in tetrahydrofuran. As a result, the yield of the product, ethyl 4-diethylamino-1-benzenesulfonylpentadienoate (Compound 1-3) was 18%.

The results of the Example and the Comparative Example confirm that, using safe reagents, the invention realizes industrial-scale economical production of δ-aminopentadienoate derivatives.

The invention claimed is:

1. A method for producing a δ-aminopentadienoate compound of the following formula (1), the method comprising the step of; reacting a streptocyanine compound of the following formula (2) with an ester compound of the following formula (3) in the presence of an organic base,

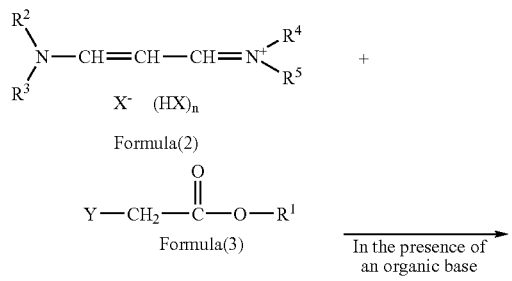

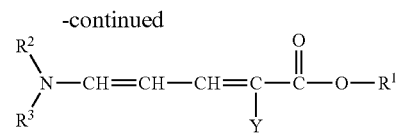

Formula(1)

wherein in formulae (1)-(3), $R^1$ is at least one selected from the group consisting of an alkyl group and an aryl group; $R^2$, $R^3$, $R^4$ and $R^5$ independently represent at least one selected from the group consisting of a hydrogen atom and an alkyl group; at least one of $R^2$ and $R^3$, and $R^4$ and $R^5$ may bond to each other to form a ring; Y represents an electron attractive group which is at least one selected from the group consisting of an alkylsulfonyl group, an arylsulfonyl group, an arylcarbonyl group, an aryloxycarbonyl group, a formyl group, a trifluoromethoxy group, a trifluoromethylthio group, an alkylcarbamoyl group, an arylcarbamoyl group, an alkylsulfinyl group, an arylsulfinyl group, an alkylsulfamoyl group, an arylsulfamoyl group, and a trifluoromethyl group; X represents an acid radical; n indicates one of 0 and a positive number of no more than 5.

2. The method for producing a δ-aminopentadienoate compound of claim 1, wherein the electron attractive group represented by Y in formula (1) is at least one selected from the group consisting of an alkanesulfonyl group, an arenesulfonyl group, an arylcarbonyl group, and an aryloxycarbonyl group.

3. The method for producing a δ-aminopentadienoate compound of claim 1, wherein the electron attractive group represented by Y in formula (1) is an arenesulfonyl group.

4. The method for producing a δ-aminopentadienoate compound of claim 1, wherein the acid radical represented by X in formula (2) is at least one selected from the group consisting of an acetate radical, a hydrochloride radical, a sulfate radical, a bromide radical, an iodide radical, a perchlorate radical, a p-toluenesulfonate radical and a methanesulfonate radical.

5. The method for producing a δ-aminopentadienoate compound of claim 2, wherein the acid radical represented by X in formula (2) is at least one selected from the group consisting of an acetate radical, a hydrochloride radical, a sulfate radical, a bromide radical, an iodide radical, a perchlorate radical, a p-toluenesulfonate radical and a methanesulfonate radical.

6. The method for producing a δ-aminopentadienoate compound of claim 1, wherein the acid radical represented by X in formula (2) is an acetate radical.

7. The method for producing a δ-aminopentadienoate compound of claim 3, wherein the acid radical represented by X in formula (2) is an acetate radical.

8. The method for producing a δ-aminopentadienoate compound of claim 1, wherein the organic base is at least one selected from the group consisting of an alkoxide, 1,8-diazabicyclo[5.4.0]undec-7-ene, 1,5-diazabicyclo[4.3.0] non-5-ene and 1,1,3,3 -tetramethylguanidine.

9. The method for producing a δ-aminopentadienoate compound of claim 1, wherein the organic base is at least one of 1,8-diazabicyclo[5.4.0]undec-7-ene and 1,5-diazabicyclo[4.3.0]non-5-ene.

10. The method for producing a δ-aminopentadienoate compound of claim 3, wherein the organic base is at least one of 1,8-diazabicyclo[5.4.0]undec-7-ene and 1,5-diazabicyclo[4.3.0]non-5-ene.

11. The method for producing a δ-aminopentadienoate compound of claim 6, wherein the organic base is at least one of 1,8-diazabicyclo[5.4.0]undec-7-ene and 1,5-diazabicyclo[4.3.0]non-5-ene.

12. The method for producing a δ-aminopentadienoate compound of claim 7, wherein the organic base is at least one of 1,8-diazabicyclo[5.4.0]undec-7-ene and 1,5-diazabicyclo[4.3.0]non-5-ene.

13. The method for producing a δ-aminopentadienoate compound of claim 1, wherein the streptocyanine compound of formula (2) is reacted with the ester compound of formula (3) in the presence of an organic solvent.

14. The method for producing a δ-aminopentadienoate compound of claim 13, wherein the streptocyanine compound of formula (2) is reacted with the ester compound of formula (3) at a temperature of from −78° C. to the boiling point of the organic solvent.

15. The method for producing a δ-aminopentadienoate compound of claim 1, wherein the molar ratio of the organic base to HX of the streptocyanine compound of formula (2) is from 0.1 to 100.

16. The method for producing a δ-aminopentadienoate compound of claim 1, wherein the molar ratio of the organic base to HX of the streptocyanine compound of formula (2) is from 0.5 to 3.

17. The method for producing a δ-aminopentadienoate compound of claim 1, wherein the molar ratio of the ester compound of formula (3) to the streptocyanine compound of formula (2) is from 0.1 to 100.

18. The method for producing a δ-aminopentadienoate compound of claim 1, wherein the molar ratio of the ester compound of formula (3) to the streptocyanine compound of formula (2) is from 0.8 to 2.

19. The method for producing a δ-aminopentadienoate compound of claim 13, wherein the ratio by mass of the organic solvent to the streptocyanine compound of formula (2) is from 0.5 to 20.

20. The method for producing a δ-aminopentadienoate compound of claim 13, wherein the organic solvent is at least one selected from the group consisting of dimethylformamide, dimethylacetamide, 1-methylpyrrolidone and dimethylsulfoxide.

21. A method for producing a δ-aminopentadienoate compound of the following formula (1), the method comprising the step of; reacting a streptocyanine compound of the following formula (2) with an ester compound of the following formula (3) in the presence of an organic base,

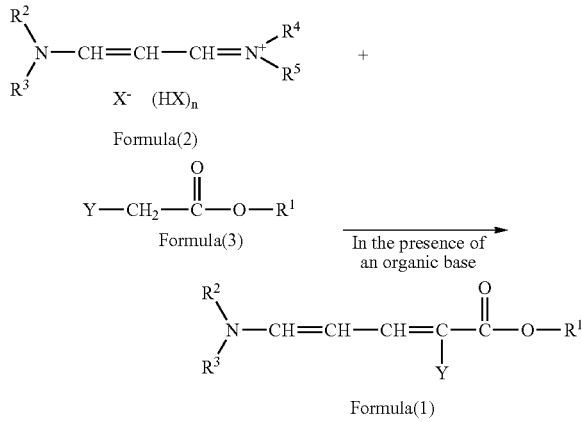

wherein in formulae (1)-(3), $R^1$ represents one of an alkyl group and an aryl group; $R^2$, $R^3$, $R^4$ and $R^5$ independently represent at least one of a hydrogen atom, ethyl, propyl, butyl, pentyl, hexyl, heptyl, octyl, nonyl and decyl; at least one of $R^2$ and $R^3$, and $R^4$ and $R^5$ may bond to each other to form a ring; Y represents an electron attractive; X represents an acid radical; n indicates one of 0 and a positive number of no more than 5.

* * * * *